US00PP26496P2

(12) United States Plant Patent
Koning

(10) Patent No.: US PP26,496 P2
(45) Date of Patent: Mar. 8, 2016

(54) *LAVANDULA* PLANT NAMED 'ANOUK DELUXE 1956'

(50) Latin Name: *Lavandula stoechas*
Varietal Denomination: Anouk Deluxe 1956

(71) Applicant: Lammert Koning, Nuis (NL)

(72) Inventor: Lammert Koning, Nuis (NL)

(73) Assignee: New Variety B.V., Kudelstaart (NL)

( * ) Notice: Subject to any disclaimer, the term of this patent is extended or adjusted under 35 U.S.C. 154(b) by 98 days.

(21) Appl. No.: 14/120,161

(22) Filed: Apr. 30, 2014

(51) Int. Cl.
*A01H 5/02* (2006.01)

(52) U.S. Cl.
USPC ..... Plt./445

(58) Field of Classification Search
USPC ..... Plt./445
See application file for complete search history.

*Primary Examiner* — Susan McCormick Ewoldt
(74) *Attorney, Agent, or Firm* — C. A. Whealy

(57) ABSTRACT

A new and distinct cultivar of *Lavandula* plant named 'Anouk Deluxe 1956', characterized by its compact and broadly upright plant habit; freely branching growth habit; dense and bushy appearance; durable narrow leaves; freely flowering habit; dark violet blue and purple-colored flowers positioned on strong and erect peduncles; and good garden performance.

1 Drawing Sheet

Botanical designation: *Lavandula stoechas.*
Cultivar denomination: 'ANOUK DELUXE 1956'.

BACKGROUND OF THE INVENTION

The present invention relates to a new and distinct *Lavandula* plant, botanically known as *Lavandula stoechas*, commonly referred to as Lavender and hereinafter referred to by the name 'Anouk Deluxe 1956'.

The new Lavender plant is a product of a planned breeding program conducted by the Inventor in Nuis, The Netherlands. The objective of the breeding program was to develop new strong *Lavandula* plants with attractive plant form and flower coloration.

The new *Lavandula* plant originated from a cross-pollination made by the Inventor during the summer of 2008 of a proprietary selection of *Lavandula stoechas* identified as code number 400, not patented, as the female, or seed, parent with *Lavandula stoechas* 'Anouk', disclosed in U.S. Plant Pat. No. 16,685, as the male, or pollen, parent. The new *Lavandula* plant was discovered and selected by the Inventor during the summer of 2009 as a single flowering plant within the progeny of the stated cross-pollination in a controlled environment in Nuis, The Netherlands.

Asexual reproduction of the new *Lavandula* plant by terminal cuttings in a controlled greenhouse environment in Nuis, The Netherlands since the autumn of 2009 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Anouk Deluxe 1956' as a new and distinct *Lavandula* plant:

1. Compact and broadly upright plant habit.
2. Freely branching growth habit; dense and bushy appearance.
3. Durable narrow leaves.
4. Freely flowering habit.
5. Dark violet blue and purple-colored flowers positioned on strong and erect peduncles.
6. Good garden performance.

Plants of the new *Lavandula* differ from plants of the female parent selection primarily in branching habit as plants of the new *Lavandula* are more freely branching than plants of the female parent selection.

Plants of the new *Lavandula* differ from plants of the male parent, 'Anouk', primarily in plant habit as plants of the new *Lavandula* are more compact and mounding than plants of 'Anouk'. In addition, plants of the new *Lavandula* flower earlier than plants of 'Anouk'.

Plants of the new *Lavandula* can be compared to plants of the *Lavandula stoechas* 'Silver Anouk', disclosed in U.S. Plant Pat. No. 20,068. In side-by-side comparisons, plants of the new *Lavandula* differ from plants of 'Silver Anouk' in the following characteristics:

1. Plants of the new *Lavandula* are more compact, bushier and denser than plants of 'Silver Anouk'.
2. Plants of the new *Lavandula* and 'Silver Anouk' differ in leaf color'.

BRIEF DESCRIPTION OF THE PHOTOGRAPH

The accompanying photograph illustrates the overall appearance of the new *Lavandula* plant showing the colors as true as it is reasonably possible to obtain in colored reproductions of this type. Colors in the photograph may differ slightly from the color values cited in the detailed botanical description which accurately describe the colors of the new *Lavandula* plant.

The photograph comprises a side perspective view of a typical flowering plant of 'Anouk Deluxe 1956' grown in a container.

DETAILED BOTANICAL DESCRIPTION

Plants used in the aforementioned photograph and following detailed description were grown in 2.3-liter containers during the spring summer in a glass-covered greenhouse in Boskoop, The Netherlands and under cultural practices typical of commercial *Lavandula* production. Plants were pinched two times and were twelve months old when the photograph and description were taken. During the production of the plants, day temperatures ranged from 14° C. to 26° C. and night temperatures ranged from 6° C. to 18° C. In the following description, color references are made to The Royal Horticultural Society Colour Chart, 2007 Edition, except where general terms of ordinary dictionary significance are used.

Botanical classification: *Lavandula stoechas* 'Anouk Deluxe 1956'.

Parentage:

*Female, or seed, parent*.—Proprietary selection of *Lavandula stoechas* identified as code number 400, not patented.

*Male, or pollen, parent*.—*Lavandula stoechas* 'Anouk', disclosed in U.S. Plant Pat. No. 16,685.

Propagation:

*Type*.—Terminal vegetative cuttings.

*Time to initiate roots, summer*.—About one week at temperatures ranging from 14° C. to 26° C.

*Time to initiate roots, winter*.—About ten days at temperatures ranging from 14° C. to 26° C.

*Time to produce a rooted young plant, summer*.—About three to four weeks at temperatures ranging from 14° C. to 26° C.

*Time to produce a rooted young plant, winter*.—About four to six weeks at temperatures ranging from 14° C. to 26° C.

*Root description*.—Fine, fibrous; white in color.

*Rooting habit*.—Freely branching; dense.

Plant description:

*Plant and growth habit*.—Herbaceous perennial; compact and broadly upright plant habit; freely branching habit, dense and bushy appearance; moderately vigorous growth habit; flowers arranged in verticillasters on crowded spikes with showy terminal flower bracts.

*Plant height*.—About 17.7 cm.

*Plant width*.—About 28.8 cm.

*Lateral branch description*.—Quantity per plant: About 17. Length, from stem to base of inflorescence: About 8.5 cm. Diameter: About 3 mm. Internode length: About 9.5 mm. Strength: Strong. Aspect: Mostly upright. Texture: Densely tomentose. Color: Close to between 145A; pubescence, close to 157A to 157D.

*Leaf description*.—Arrangement: Opposite, simple; sessile. Length: About 4.2 cm. Width: About 6 mm. Shape: Lanceolate. Apex: Acute. Base: Cuneate. Margin: Entire; revolute. Texture, upper and lower surfaces: Moderately tomentose. Fragrance: Strongly aromatic, pungent. Venation pattern: Pinnate. Color: Developing leaves, upper surface: Close to 137B to 137C. Developing leaves, lower surface: Close to 138C. Fully expanded leaves, upper surface: Close to N137B; venation, close to N137B; pubescence, close to 157A to 157B. Fully expanded leaves, lower surface: Close to 137B to 137C; venation, close to 143C; pubescence, close to 157A to 157B.

Flower description:

*Flower type, arrangement and habit*.—Small single flowers arranged in compact verticillasters on crowded spikes; freely flowering, about 150 flowers developing per inflorescence; flowers tubular with five lobes; inflorescences with showy terminal bracts.

*Natural flowering season*.—Long flowering period; continuous from late spring into the late summer in The Netherlands.

*Flower longevity on the plant*.—Individual inflorescences last about ten days on the plant; flowers not persistent.

*Fragrance*.—None detected.

*Flower buds*.—Length: About 7 mm. Diameter: About 3 mm. Shape: Oblong. Color: Close to N77A; apex, close to 59A; base, close to 145A to 145B.

*Inflorescence size*.—Height: About 5.1 cm. Diameter, apex: About 1.7 cm. Diameter, base: About 2.8 cm.

*Flower size*.—Diameter: About 3 mm. Depth (height): About 7 mm.

*Petals*.—Quantity and arrangement: Five, fused into a tube. Length: About 7 mm to 8 mm. Width: About 3 mm. Shape: Roughly spatulate; lower 62.5% fused into a tube. Apex: Rounded. Margin: Entire. Texture, upper and lower surfaces: Smooth, glabrous. Color: When opening, upper and lower surfaces: Close to N92A; tube, close to N155A; base, close to 145D. Fully opened, upper and lower surfaces: Close to N92A; tube, close to N155A; base, close to 145D.

*Terminal flower bracts*.—Quantity and arrangement: About 7 to 15 positioned at inflorescence apex. Length: About 2.2 cm. Width: About 8 mm. Shape: Narrowly oblanceolate. Apex: Broadly acute. Base: Cuneate. Margin: Entire; slightly undulate. Texture, upper and lower surfaces: Smooth, glabrous. Color, upper and lower surfaces: Close to 79C.

*Flower bracts*.—Quantity and arrangement: Each whorl of five flowers is subtended by a single flower bract. Length: About 8 mm. Width: About 7 mm. Shape: Broadly rhomboidal. Apex: Aristate. Base: Cuneate. Margin: Entire. Texture, upper and lower surfaces: Moderately tomentose. Color, upper and lower surfaces: Close to 71C; venation, close to N79A.

*Sepals*.—Quantity and arrangement: Five, fused into a campanulate tube. Length: About 6 mm. Width: About 1 mm. Shape: Lanceolate. Apex: Acute. Margin: Entire. Texture, upper and lower surfaces: Densely tomentose. Color: When opening, upper and lower surfaces: Close to N77A; base, close to 145A to 145B. Fully opened, upper and lower surfaces: Close to N77A; base, close to 145C.

*Peduncles*.—Length: About 5.8 cm. Diameter: About 2 mm. Aspect: Mostly upright. Strength: Strong. Texture: Densely pubescent. Color: Close to 143B and 144B; pubescence, close to 157C to 157D.

*Reproductive organs*.—Stamens: Quantity per flower: Four. Filament length: About 1.5 mm. Anther shape: Reniform. Anther length: About 0.5 mm. Anther color: Close to 85B to 85D. Pollen amount: Moderate. Pollen color: Close to 22A. Pistils: Quantity per flower: One. Pistil length: About 4 mm. Stigma shape: Club-shaped. Stigma color: Close to N186A. Style length: About 3.5 mm. Style color: Close to 155C. Ovary color: Close to 143B.

*Seeds and fruits*.—Seed and fruit production has not been observed on plants of the new *Lavandula*.

Disease & pest resistance: Plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40° C. and to be hardy to USDA Hardiness Zone 7.

It is claimed:

1. A new and distinct *Lavandula* plant named 'Anouk Deluxe 1956' as illustrated and described.

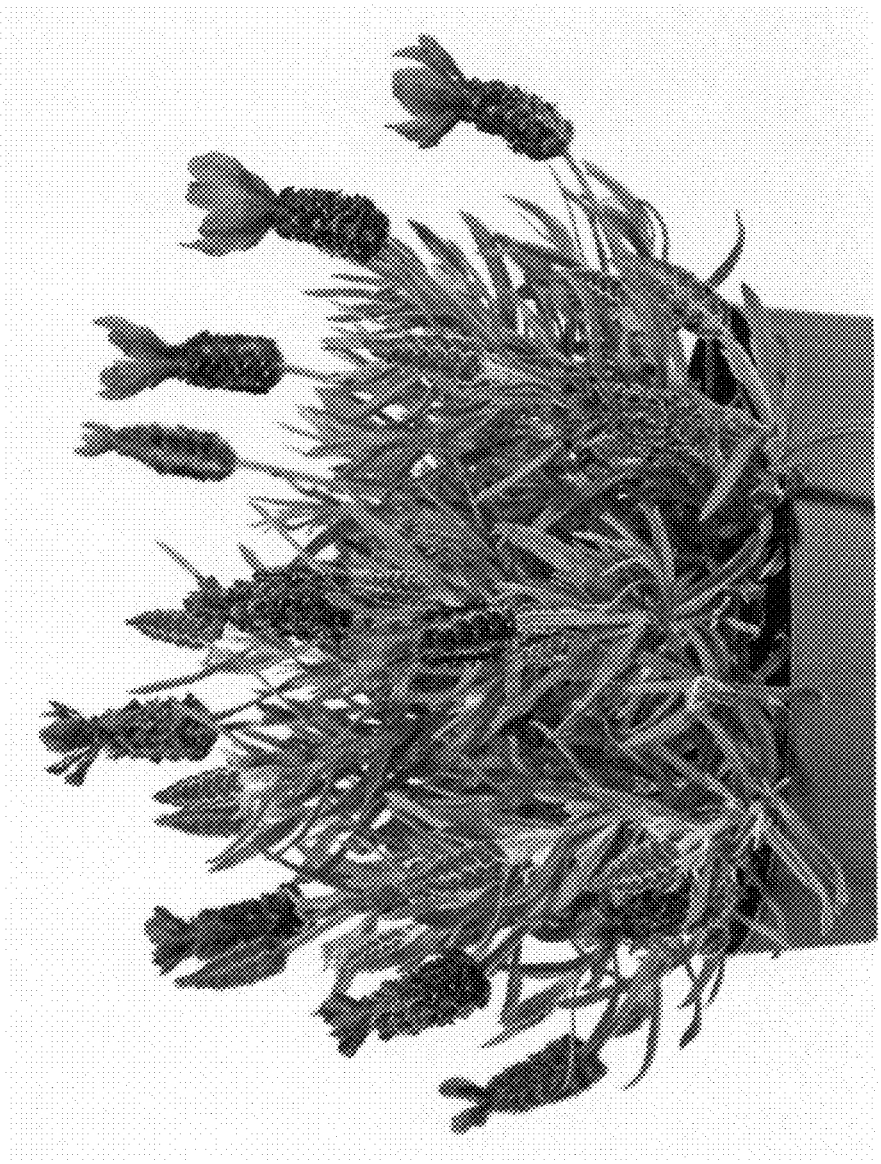

* * * * *